United States Patent [19]

Hashem et al.

[11] Patent Number: 4,994,577
[45] Date of Patent: Feb. 19, 1991

[54] QUATERNIZED SILICONES

[75] Inventors: Mohamed M. Hashem, Wayne; James H. Merrifield, Landing, both of N.J.

[73] Assignee: Rhone-Poulenc Specialty Chemicals, L. P., Monmouth Jct., N.J.

[21] Appl. No.: 402,413

[22] Filed: Sep. 5, 1989

[51] Int. Cl.[5] .............................................. C07F 7/02
[52] U.S. Cl. ................................................. 548/406
[58] Field of Search .......................... 548/406; 514/63; 252/51, 542

[56] References Cited

U.S. PATENT DOCUMENTS 4,059,581 11/1977 Prokai ................................ 542/406

*Primary Examiner*—Mukund J. Shaw
*Assistant Examiner*—E. C. Ward
*Attorney, Agent, or Firm*—Paul J. Juettner; John A. Shedden

[57] ABSTRACT

The invention relates to the addition product formed from the reaction of a tertiary amino substituted alkyl lactam having the formula

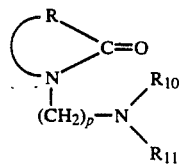

and a haogenated silicone having the formulae

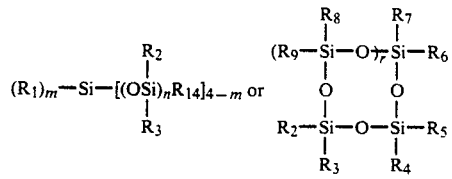

wherein m has a value of from 1 to 3; n has a value of from 1 to 100; r has a value of from 0 to 3, $R_{14}$ is

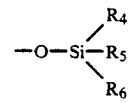

or
$R_{15}$
$R_1$, $R_2$, $R_3$, $R_4$, $R_5$, $R_6$, $R_7$, $R_8$, $R_9$ and $R_{15}$ are each individually alkyl, alkoxy, haloalkyl, phenyl, benzyl, haloalkyl-phenyl, halophenyl or mixtures thereof and wherein at least one of said substituents bonded to a silicon atom is a radical having a haloalkyl group;

R is alkylene having from 3 to 8 carbon atoms, optionally substituted with lower alkyl, carboxyl, halo or

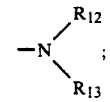

$R_{10}$, $R_{11}$, $R_{12}$ and $R_{13}$ are each independently lower alkyl and p has a value of from 1 to 6.

9 Claims, No Drawings

QUATERNIZED SILICONES

In one aspect this invention relates to novel quaternized silicone compounds. In other aspects, the invention relates to the preparation and the use of the quaternized silicone compounds described herein.

It is an object of this invention to provide novel compounds which are keratin substantive and which provide superior hair and skin conditioning properties.

Another object of this invention is to provide non-yellowing quaternized silicone compounds having enduring antistatic properties.

Another object is to provide novel quaternized silicone compounds suitable for coating a substrate to prevent dehydration of cellular material or to prevent static build-up in textiles or in the molding processing of plastics.

Still another object of the invention is to provide a process for obtaining quaternized silicones by an economical and commercially feasible method.

Another object is to provide commercial products which have been treated with the quaternized silicones of this invention.

These and other objects of the invention will become apparent from the following description and disclosure.

This invention is directed to an addition product derived from contacting a halogenated silicone having the formula

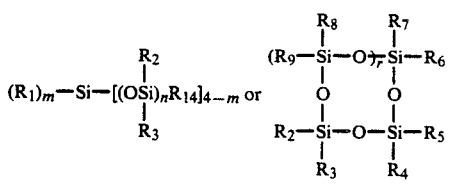

and a tertiary amine substituted N-alkyl lactam having the formula

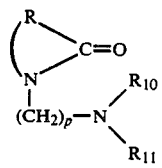

wherein m has a value of from 1 to 3; n has a value of from 1 to 100; r has a value of from 0 to 3; $R_{14}$ is

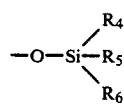

or $R_{15}$ $R_1$, $R_2$, $R_3$, $R_4$, $R_5$, $R_6$, $R_7$, $R_8$, $R_9$ and $R_{15}$ are each independently alkyl, alkoxy, haloalkyl, phenyl, benzyl, haloalkyl-phenyl, halophenyl or mixtures thereof and wherein at least one of $R_1$, $R_2$, $R_3$, $R_4$, $R_5$, $R_6$, $R_7$, $R_8$ and $R_9$, is a radical containing a haloalkyl group; R is alkyl having from 3 to 8 carbon atoms, optionally substituted with lower alkyl, halo, carboxyl or

$R_{10}$, $R_{11}$, $R_{12}$ and $R_{13}$ are each independently lower alkyl and p has a value of from 1 to 6.

The products of the addition reaction of this invention are defined by the following formulae

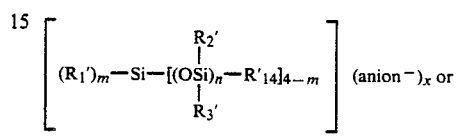

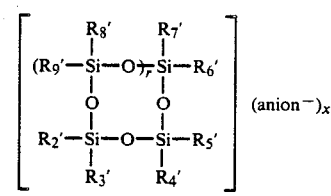

wherein
m, n, and r are as defined above; $R'_1$, $R'_2$, $R'_3$, $R'_4$, $R'_5$, $R'_6$, $R'_7$, $R'_8$, $R'_9$, $R'_{14}$ and $R'_{15}$ correspond to $R_1$, $R_2$, $R_3$, $R_4$, $R_5$, $R_6$, $R_7$, $R_8$, $R_9$, $R_{14}$ and $R_{15}$ except that, where $R_1$, $R_2$, $R_3$, $R_4$, $R_5$, $R_6$, $R_7$, $R_8$, $R_9$, $R_{14}$ or $R_{15}$ is a radical containing a haloalkyl group, at least one of the halogen atoms in the haloalkyl group is replaced in the corresponding $R'_1$, $R'_2$, $R'_3$, $R'_4$, $R'_5$, $R'_6$, $R'_7$, $R'_8$, $R'_9$, $R'_{14}$ and $R'_5$ with the radical

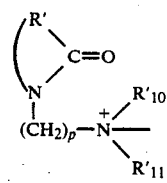

where p is as defined above; R', $R'_{10}$ and $R'_{11}$ correspond to R, $R_{10}$ and $R_{11}$; x is equal to the number of quaternized nitrogen atoms in the product molecule and the anion is a halide anion, such as Cl, Br, I or the anion salt conjugate base of a strong acid, which includes sulfur-, phosphorous-, or boron-containing salts such as the sulfate, sulfonate, tosylate, phosphate and tetrafluoroborate anion salts derived from anion exchange with the halide anion.

A species of these quaternized silicones includes mixtures of non-quaternized and quaternized silicone units in a polymeric silicone chain as illustrated by the formula:

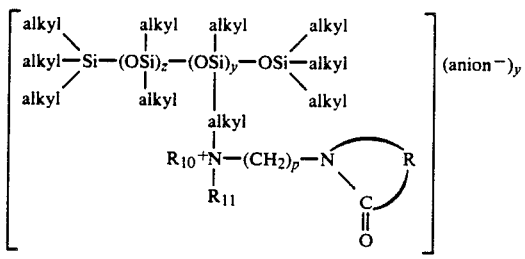

wherein the mole ratio of y to z is between about 1:3 and about 1:100, preferably between about 1:5 and about 1:20.

The structure of these polymers may occur in block, alternating or random form.

Examples of other species include

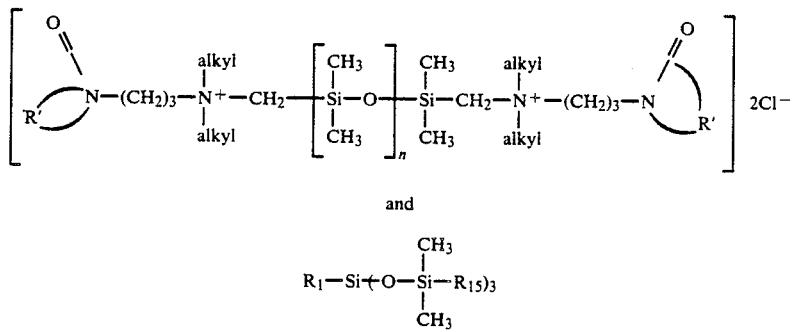

and $$R_1-Si+O-Si-R_{15})_3$$
$$\phantom{R_1-Si+O-}\overset{CH_3}{\underset{CH_3}{|}}$$

and modifications thereof.

These compounds are derived from the corresponding silicone reactants having haloalkyl groups bonded to the silicone group of expression "y".

The preferred halogenated silicone reactants are substantially linear polysilicones containing from 1 to 25, most preferably from 1 to 10, haloalkyl- containing radicals as defined above; most preferably those wherein the haloalkyl group contains from 1 to 4 carbon atoms and less than 4 halogen atoms. The preferred lactam coreactant is an N-lower alkyl tert-amino pyrrolidone optionally substituted on the hetero ring with an alkyl or carboxyl group.

As used herein, the terms halo, halogen or halide are intended to exclude fluoro, fluorine or fluoride, all other halides comprising Cl, Br and I are included.

The process for preparing the present compounds is both economical and commercially feasible. In general, the halogenated silicone and the lactam coreactant are contacted at a temperature of between about 60° C. and about 130° C., preferably at a temperature between about 80° C. and about 100° C. for a period of from about 1 to about 50 hours, preferably from about 5 to about 20 hours, under from about 1 to about 5 atmospheres pressure, preferably at ambient pressure developed in the system. The mole ratio of lactam per haloalkyl- containing radical of the silicon coreactant can vary between about 1:1 and about 1:3, preferably between about 1:1 and about 1:1.5. Ideally, the ratio is maintained as close to 1:1 as convenient during the reaction.

The addition reaction is carried out under anhydrous conditions, generally under a blanket of an inert gas, such as nitrogen. Although solvents need not be employed, at the higher temperatures within the above range, it may be convenient to dilute the reactants with a suitable inert solvent such as a $C_2$ to $C_4$ alcohol, tetrahydrofuran, xylene, cyclohexane, etc. Under pressurized conditions, lower boiling solvents such as acetone, methyl ethyl ketone and methanol also can be employed. Mixtures of inert solvents are also contemplated. The products of the invention prepared in the absence of solvent are generally obtained as solids which can be solubilized before incorporation into a commercial formulation, such as a hair or skin treating formulation, a coating formulation, a mold release formulation, etc, if desired.

To hasten the reaction, e.g. when operating at lower temperatures, catalysts such as an ion exchange resin can be employed. Examples of suitable catalysts include silver nitrate, silver hexafluorophosphate and silver tetrafluoroborate. Under the above conditions, the products of the reaction may be added directly to cosmetic, fabric coating, mold coating or other formulations. The products of this invention possess excellent substantivity to skin, hair, plastics and textiles. Since the products are non-yellowing, they are superior candidates for hair care to provide enduring luster, shine and other conditioning effects. The present compounds also possess excellent antistatic properties and are beneficially employed on textiles, plastics, or human hair, etc. and as a mold release agent to prevent static build-up. In the present compounds the quaternized group possesses the ability to disperse static charges while the silicon moiety prevents static build-up; hence, the antistatic properties imparted by these compounds has a lasting effect. The present products also can be used as a foiliant spray to prevent dehydration under drought conditions and to maintain shine and luster to leaves. These and other benefits and advantages will become apparent from the present disclosure.

Having thus described the invention, reference is now had to the accompanying examples which illustrate preferred embodiments but which are not to be construed as limiting to the scope of the invention as more broadly described above and in the appended claims.

EXAMPLE 1

A 250 ml three neck round bottom flask fitted with a thermometer, a nitrogen inlet and a mechanical stirrer is charged with 335 grams (0.25 mole) of silicone having the formula

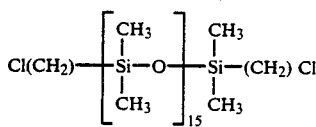

and 85 grams (0.5 mole) of 1-[3-(dimethylamino)-propyl]-2-pyrrolidone having the formula

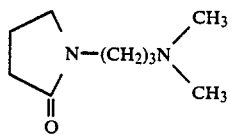

The flask is purged with nitrogen and heated to 90° C. for 6 hours while stirring, after which the reaction is cooled and transferred to a separatory funnel where 200 ml of acetonitrile and 200 ml of hexane are added. The mixture is shaken and two layers are formed upon standing. The acetonitrile layer is collected and the solvent removed by vacuum stripping to provide the desired product having the formula

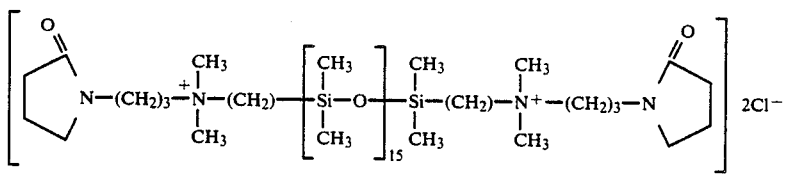

EXAMPLE 2

A 250 ml three neck round bottom flask fitted with a thermometer, a nitrogen inlet and a mechanical stirrer is charged with 154 grams (0.15 mole) of silicone having the formula

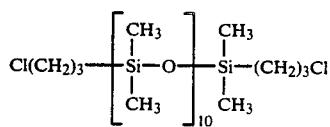

and 65 grams (1.35 mole) of 1-[3-(dimethylamino)-propyl]-2-pyrrolidone carboxylate having the formula

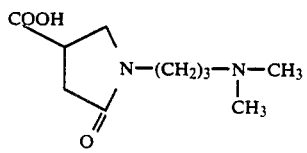

The flask is purged with nitrogen and heated to 90° C. for 6 hours while stirring, after which the reaction is cooled and transferred to a separatory funnel where 200 ml of acetonitrile and 200 ml of hexane are added. The mixture is shaken and two layers are formed upon standing. The acetonitrile layer is collected and the solvent removed by vacuum stripping to provide the desired product having the formula

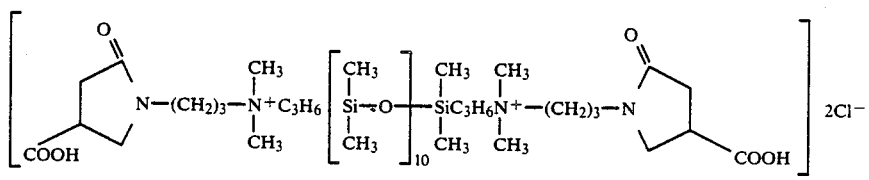

EXAMPLE 3

A 250 ml three neck round bottom flask fitted with a thermometer, a nitrogen inlet and a mechanical stirrer is charged with 212 grams (0.2 mole) of silicone having the formula

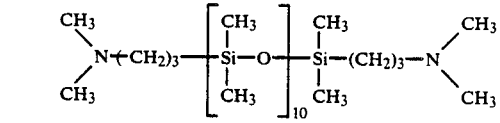

and 27 grams (0.4 mole) of N-chloromethyl-2-pyrrolidone having the formula

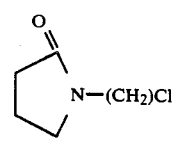

The flask is purged with nitrogen and heated to 90° C. for 6 hours while stirring, after which the reaction is cooled and transferred to a separatory funnel where 200 ml of acetonitrile and 200 ml of hexane are added. The mixture is shaken and two layers are formed upon standing. The acetonitrile layer is collected and the solvent removed by vacuum stripping to provide the desired product having the formula

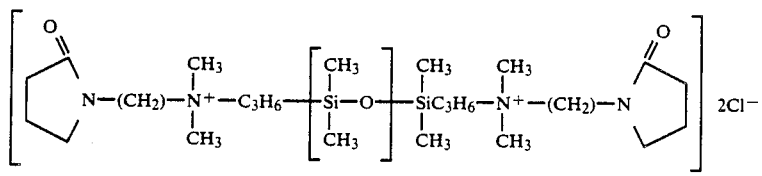

EXAMPLE 4

The general procedure outlined in Example 1 is repeated, except that 100 grams of the silicone

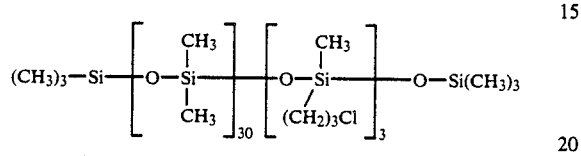

and 19.0 grams of 1[3-(dimethylamino)propyl]-2-pyrrolidone are substituted therein. The resulting mixture is reacted at 100° C. for 24 hours. The residue is dissolved in an equal weight of isopropanol to give a clear homogeneous product solution.

The product of this example is illustrated by the formula

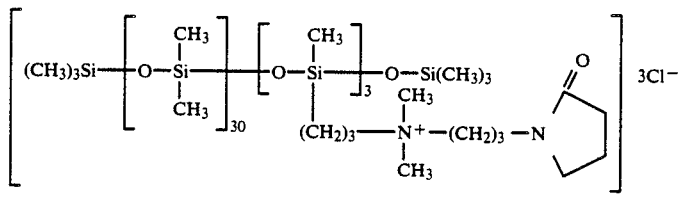

The products of this invention, particularly those containing from 5 to 100 silicon oxide units, can be added to a commercial formulation in a dry particulate state or in solution or dispersion with an inert solvent or dispersing agent; water being a suitable solvent or dispersant depending on the degree of quaternization. Generally the concentration of the quaternized product with respect to the total composition can vary between about 0.1% and about 15% by weight depending upon the compound selected and the desired function in a given formulation. The unique properties of the present products impart superior hair luster, skin softness, antistatic properties hydrolysis resistant coatings and mold release enhancement when incorporated into dry mixture, solution, gel or cream formulations requiring these attributes.

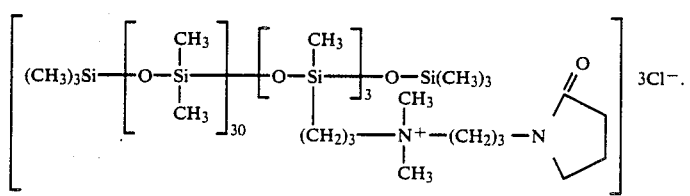

What is claimed is:

1. The addition product derived from the reaction of a tertiary amino substituted -2-pyrrolidone having the formula

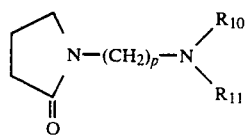

wherein the pyrrolidone ring is optionally substituted with carboxyl or lower alkyl, and a halogenated silicone having the formulae

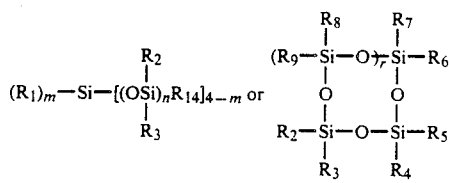

wherein m has a value of from 1 to 3; n has a value of from 1 to 100; r has a value of from 0 to 3, $R_{14}$ is

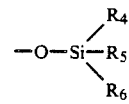

$R_1$, $R_2$, $R_3$, $R_4$, $R_5$, $R_6$, $R_7$, $R_8$, $R_9$ and $R_{15}$ are each individually alkyl, alkoxy, haloalkyl, phenyl, benzyl, haloalkyl-phenyl, halophenyl or mixtures thereof and wherein from 1 to 10 of $R_1$, $R_2$, $R_3$, $R_4$, $R_5$, $R_6$, $R_7$, $R_8$, and $R_9$ bonded to a silicon atom is a radical having a haloalkyl group wherein the halogen atom is selected from Cl, Br and I, the alkyl has from 1 to 4 carbon atoms and the group has less than 4 halogen atoms;

$R_{10}$ and $R_{11}$ are each independently lower alkyl and p has a value of from 1 to 6.

2. A quaternized silicone compound having the formulae

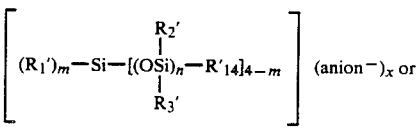

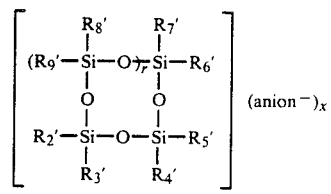

wherein m, n, and r are as defined above; $R'_1$, $R'_2$, $R'_3$, $R'_4$, $R'_5$, $R'_6$, $R'_7$, $R'_8$, $R'_9$, $R'_{14}$ and $R'_{15}$ correspond to $R_1$, $R_2$, $R_3$, $R_4$, $R_5$, $R_6$, $R_7$, $R_8$, $R_9$, $R_{14}$ and $R_{15}$ except that, where $R_1$, $R_2$, $R_3$, $R_4$, $R_5$, $R_6$, $R_7$, $R_8$, $R_9$, $R_{14}$ or $R_{15}$ is a radical containing a haloalkyl group, where the halogen and alkyl groups are as defined above; at least one of the halogen atoms in the haloalkyl group is replaced in the corresponding $R'_1$, $R'_2$, $R'_3$, $R'_4$, $R'_5$, $R'_6$, $R'_7$, $R'_8$, $R'_9$, $R'_{14}$ and $R'_{15}$ with the quaternized pyrrolidone radical where the pyrrolidone ring is optionally substituted with carboxyl or lower alkyl and p is as defined above; $R'_{10}$ and $R'_{11}$ correspond to $R_{10}$ and $R_{11}$; x is equal to the number of quaternized nitrogen atoms in the product molecule and the anion is a halide anion, such as Cl, Br, I or the anion salt conjugate base of a strong acid.

3. The compound of claim 2 having the formula

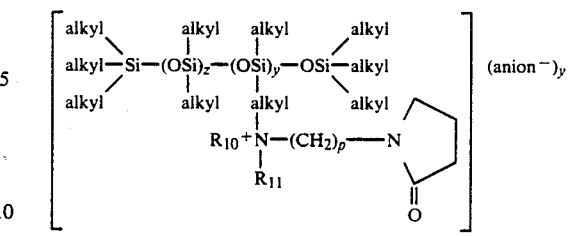

wherein the mole ratio of y to z is between about 1:3 and about 1:100, preferably between about 1:5 and about 1:20.

4. The compound of claim 2 having the formula

5. The compound of claim 1, the haloalkyl silicone having the formula

6. The compound having the formula

7. The compound having the formula

8. The compound having the formula

9. The compound having the formula